US006610043B1

(12) United States Patent  
Ingenito

(10) Patent No.: US 6,610,043 B1
(45) Date of Patent: Aug. 26, 2003

(54) TISSUE VOLUME REDUCTION

(75) Inventor: Edward P. Ingenito, Kingston, MA (US)

(73) Assignee: Bistech, Inc., Woburn, MA (US)

( * ) Notice: Subject to any disclaimer, the term of this patent is extended or adjusted under 35 U.S.C. 154(b) by 0 days.

(21) Appl. No.: 09/379,460

(22) Filed: Aug. 23, 1999

(51) Int. Cl.$^7$ .............................................. A61M 31/00
(52) U.S. Cl. ...................................... 604/514; 128/898
(58) Field of Search ........................... 604/19, 48, 500, 604/514, 93.01, 28, 35, 518, 522; 128/898; 514/802; 530/381, 382

(56) References Cited

U.S. PATENT DOCUMENTS

| | | | |
|---|---|---|---|
| 4,886,496 A | | 12/1989 | Conoscenti et al. |
| 5,423,312 A | | 6/1995 | Siegmund et al. |
| 5,437,292 A | | 8/1995 | Kipshidze et al. |
| 5,583,114 A | | 12/1996 | Barrows et al. |
| 5,728,132 A | | 3/1998 | Van Tassel et al. |
| 5,728,751 A | | 3/1998 | Patnaik |
| 5,733,545 A | | 3/1998 | Hood, III |
| 5,739,288 A | * | 4/1998 | Edwardson et al. |
| 5,773,418 A | | 6/1998 | Edwardson et al. |
| 5,782,748 A | | 7/1998 | Palmer et al. |
| 5,814,022 A | * | 9/1998 | Antanavich et al. |
| 5,836,905 A | * | 11/1998 | Lemelson et al. |
| 6,117,425 A | * | 9/2000 | MacPhee et al. |
| 6,287,290 B1 | * | 9/2001 | Perkins et al. |

FOREIGN PATENT DOCUMENTS

| | | |
|---|---|---|
| EP | 0 303 756 | 2/1989 |
| WO | WO 95/13748 | 5/1995 |
| WO | WO 97/01989 | 1/1997 |
| WO | WO 97/33633 | 9/1997 |
| WO | WO97/33633 | 9/1997 |
| WO | WO 97/42986 | 11/1997 |
| WO | WO 97/46632 | 12/1997 |
| WO | WO 99/25782 | 5/1999 |
| WO | WO 01/02042 | 1/2001 |

OTHER PUBLICATIONS e Emphysema, The Journal of Thoracic and Cardiovascualr Surgery, Nov. 1996.*
Cooper et al., J. Thorac. Cardiovasc. Surg. 109:106–116, 1995.
Cooper et al., J. Thorac. Cardiovasc. Surg. 112:1319–1329, 1996.
Gibson et al., Am. Rev. Resp. Dis. 120:799–811, 1979.
Hoppin, Am. J. Resp. Crit. Care Med. 155:520–525, 1997.
Katloff et al., Chest 110:1399–1406, 1996.
Swanson et al., J. Am. Coll. Surg. 185:25–32, 1997.
Baumann et al., *Ann. Thorac. Surg.* 64(1):230–233, 1997.
Foucher et al., *Eur. Respir J.,* 9(10):2181–2182, 1996.
Hamamoto et al., *Kekkaku (Japan),* 64(11):713–719, 1989.
Hirao et al., *Nippon Kyobu Geka Gakkai Zasshi (Japan)* 42(11):2144–2149, 1994.
Ikushima et al., *J. Jpn Assoc. Thorac. Surg.* 36(11):2521–2524, 1988.
Kawamata et al., *Kyobu Geka (Japan),* 51(2):165–167, 1998.
Klepetko et al., *Chirurg (Germany),* 67(12):1215–1221, 1996.
Koyama et al., *ACTA Haematol. Jpn.* 51(4):808–815, 1998.
Matthew et al., *Ann. Thorac. Surg.* 50(1):40–43, 1990.

(List continued on next page.)

Primary Examiner—Brian L. Casler
Assistant Examiner—Catherine Serke
(74) Attorney, Agent, or Firm—Fish & Richardson P.C.

(57) ABSTRACT

Devices, compositions, and methods for achieving non-surgical lung volume reduction (e.g., bronchoscopic lung volume reduction (BLVR)) are described. BLVR can be carried out by collapsing a region of the lung, adhering one portion of the collapsed region to another, and promoting fibrosis in or around the adherent tissue.

11 Claims, 9 Drawing Sheets

OTHER PUBLICATIONS

Nakamura et al., *Kyobu Geka (Japan)*, *50*(7):589–593, 1997.
Nonaka et al., *Kyobu Geka (Japan)* *45*(11):975–978, 1992.
Regel et al., *surg. Endosc. (Germany, West)* *4*(1):31–35, 1990.
Samuels et al., *Chest 109*(6):1653–1655, 1996.
Scheyer et al., *Surg. Endosc. (Germany)*, *10*(5):501–503, 1996.

Sprung et al., *Anaesthesia (England)* *52*(12):1207–1211, 1997.

Sznajder et al. *J. Appl. Physiol. 67*(2):817–823, 1989.

Takenouchi et al., *Kyobu Geka (Japan)* *50*(3):243–246, 1997.

Vaca et al., *Am. J. Crit. Care,* *5*(6):412–419, 1996.

* cited by examiner

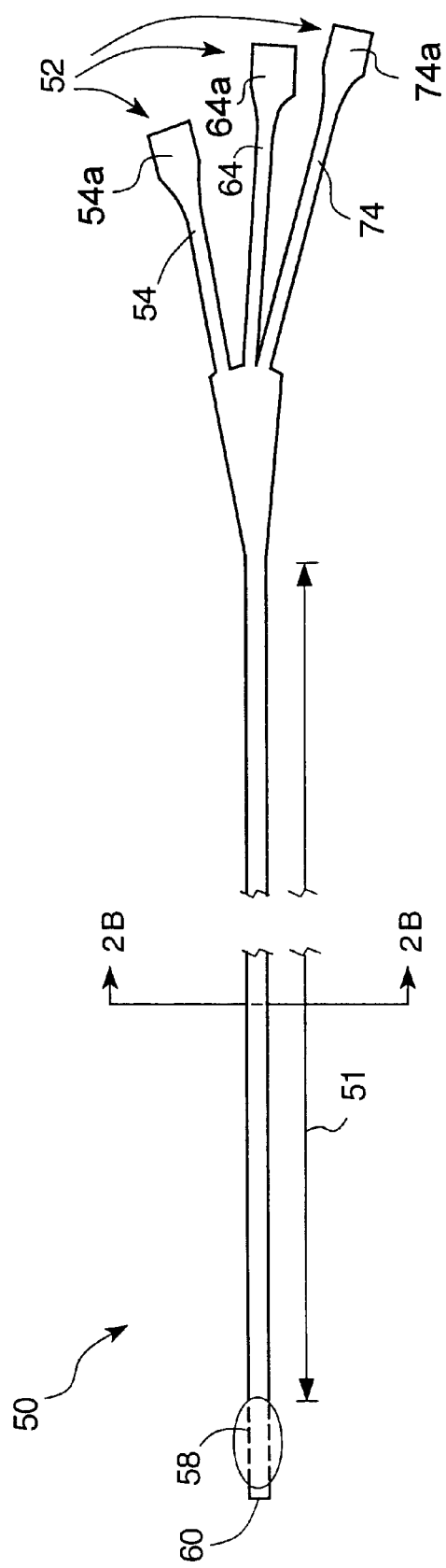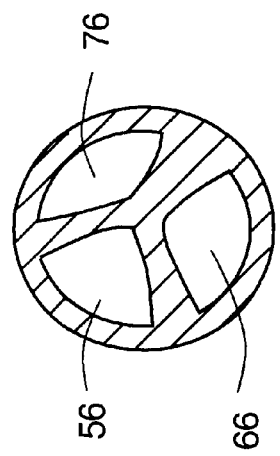
FIG. 2A
FIG. 2B

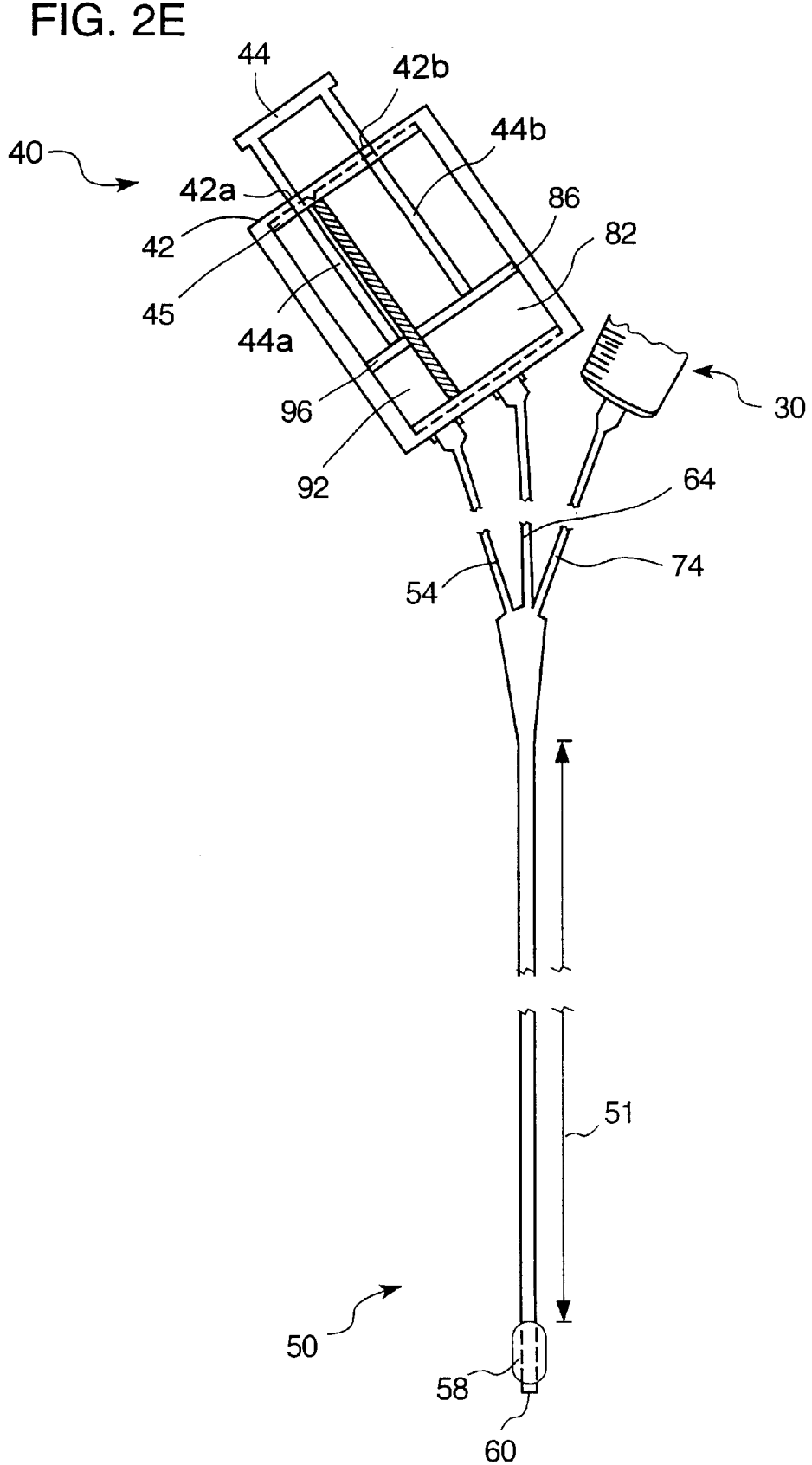

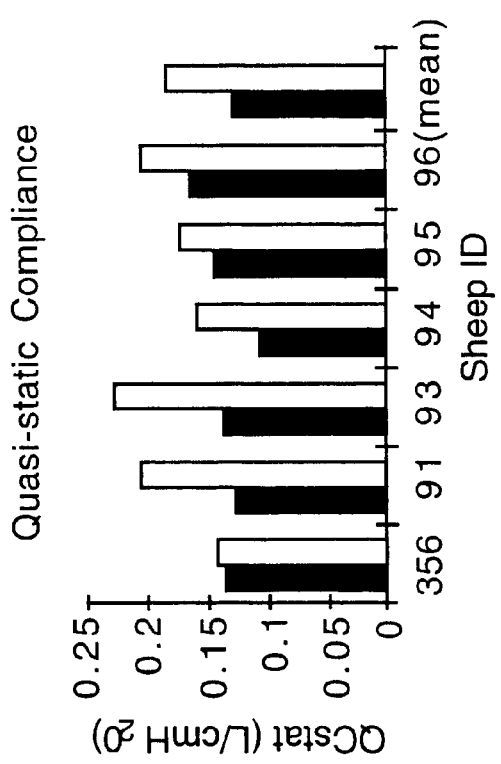
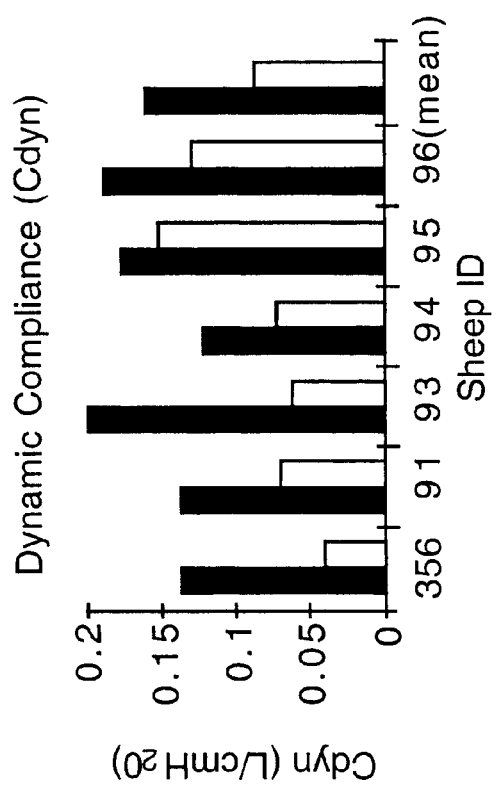

TISSUE VOLUME REDUCTION

BACKGROUND OF THE INVENTION

The field of the invention is tissue volume reduction, for example, lung volume reduction.

End stage emphysema can be treated with lung volume reduction surgery (LVRS) (see, e.g., Cooper et al., *J. Thorac. Cardiovasc. Surg.* 109:106–116, 1995). While it may seem counter-intuitive that respiratory function would be improved by removing part of the lung, excising over-distended tissue (as seen in patients with heterogeneous emphysema) allows adjacent regions of the lung that are more normal to expand. In turn, this expansion allows for improved recoil and gas exchange. Even patients with homogeneous emphysema benefit from LVRS because resection of abnormal lung results in overall reduction in lung volumes, an increase in elastic recoil pressures, and a shift in the static compliance curve towards normal (Hoppin, *Am. J. Resp. Crit. Care Med.* 155:520–525, 1997).

While many patients who have undergone LVRS experience significant improvement (Cooper et al., *J. Thorac. Cardiovasc. Surg.* 112:1319–1329, 1996), they have assumed substantial risk. LVRS is carried out by surgically removing a portion of the diseased lung, which has been accessed either by inserting a thoracoscope through the chest wall or by a more radical incision along the sternum (Katloff et al., *Chest* 110:1399–1406, 1996). Thus, gaining access to the lung is traumatic, and the subsequent procedures, which can include stapling the fragile lung tissue, can cause serious post-operative complications.

SUMMARY OF THE INVENTION

The invention features devices, compositions, and methods for achieving non-surgical lung volume reduction. In one aspect, the methods are carried out using a bronchoscope, which completely eliminates the need for surgery because it allows the tissue reduction procedure to be performed through the patient's trachea and smaller airways. In this approach, bronchoscopic lung volume reduction (BLVR) is performed by collapsing a region of the lung, adhering one portion of the collapsed region to another, and promoting fibrosis in or around the adherent tissue.

Preferred embodiments may include one or more of the following features.

There are numerous ways to induce lung collapse. For example, a material that increases the surface tension of fluids lining the alveoli (i.e., a material that can act as an anti-surfactant) can be introduced through the bronchoscope (preferably, through a catheter lying within the bronchoscope). The material can include fibrinogen, fibrin, or biologically active fragments thereof. Lung collapse can also be induced by blocking air flow into and out of the region of the lung that is targeted for collapse. This is achieved by inserting a balloon catheter through the bronchoscope and inflating the balloon so that it occludes the bronchus or bronchiole into which it has been placed.

Similarly, there are numerous ways to promote adhesion between one portion of the collapsed lung and another. If fibrinogen is selected as the anti-surfactant, adhesion is promoted by exposing the fibrinogen to a fibrinogen activator, such as thrombin, which cleaves fibrinogen and polymerizes the resulting fibrin. Other substances, including thrombin receptor agonists and batroxobin, can also be used to activate fibrinogen. If fibrin is selected as the anti-surfactant, no additional substance or compound need be administered; fibrin can polymerize spontaneously, thereby adhering one portion of the collapsed tissue to another.

Fibrosis is promoted by providing one or more polypeptide growth factors together with one or more of the anti-surfactant or activator substances described above. The growth factors can be selected from the fibroblast growth factor (FGF) family or can be transforming growth factor beta-like (TGFβ-like) polypeptides.

The compositions described above can also contain one or more antibiotics to help prevent infection. Alternatively or in addition, antibiotics can be administered via other routes (e.g., they may be administered orally or intramuscularly).

Other aspects of the invention include the compositions described above for promoting collapse and/or adhesion, as well as devices for introducing the composition into the body. For example, in one aspect, the invention features physiologically acceptable compositions that include a polypeptide growth factor or a biologically active fragment thereof (e.g., a platelet-derived growth factor, a fibroblast growth factor (FGF), or a transforming growth factor-β-like polypeptide) and fibrinogen, or a fibrin monomer (e.g., a fibrin I monomer, a fibrin II monomer, a des BB fibrin monomer, or any mixture or combination thereof), or a fibrinogen activator (e.g., thrombin). The fibrinogen, fibrin monomers, and fibrinogen activators useful in BLVR can be biologically active mutants (e.g., fragments) of these polypeptides.

In another aspect, the invention features devices for performing non-surgical lung volume reduction. For example, the invention features a device that includes a bronchoscope having a working channel and a catheter that can be inserted into the working channel. The catheter can contain multiple lumens and can include an inflatable balloon. Another device for performing lung volume reduction includes a catheter having a plurality of lumens (e.g., two or more) and a container for material having a plurality of chambers (e.g., two or more), the chambers of the container being connectable to the lumens of the catheter. These devices can also include an injector to facilitate movement of material from the container to the catheter.

BLVR has several advantages over standard surgical lung volume reduction (LVRS). BLVR should reduce the morbidity and mortality known to be associated with LVRS (Swanson et al., *J. Am. Coll. Surg.* 185:25–32, 1997). Atrial arrhythmias and prolonged air leaks, which are the most commonly reported complications of LVRS, are less likely to occur with BLVR because BLVR does not require stapling of fragile lung tissue or surgical manipulations that irritate the pericardium. BLVR may also be considerably less expensive than SLVR, which currently costs between approximately $18,000 and $26,000 per case. The savings would be tremendous given that emphysema afflicts between two and six million patients in America alone. In addition, some patients who would not be candidates for LVRS (due, e.g., to their advanced age) may undergo BLVR. Moreover, should the need arise, BLVR affords patients an opportunity to undergo more than one volume reduction procedure. While repeat surgical intervention is not a viable option for most patients (because of pleural adhesions that form following the original procedure), no such limitation should exist for patients who have undergone BLVR.

Other features and advantages of the invention will be apparent from the following detailed description, and from the claims.

BRIEF DESCRIPTION OF THE DRAWINGS

FIG. 2a illustrates a catheter that can be inserted through a bronchoscope.

FIG. 2b is a cross-sectional view through the shaft of the catheter illustrated in FIG. 2a.

FIG. 2c illustrates a cartridge that can be attached to the catheter illustrated in FIG. 2a.

FIG. 2e illustrates the catheter of FIG. 2a assembled with the cartridge of FIG. 2c, the injector of FIG. 2d, and a leur-lock, air-filled syringe.

FIGS. 5a and 5b are bar graphs depicting dynamic (FIG. 5a) and quasi-static (FIG. 5b) compliance 3 months after sheep were exposed to Papain. n=6.

DETAILED DESCRIPTION

Figure 1:
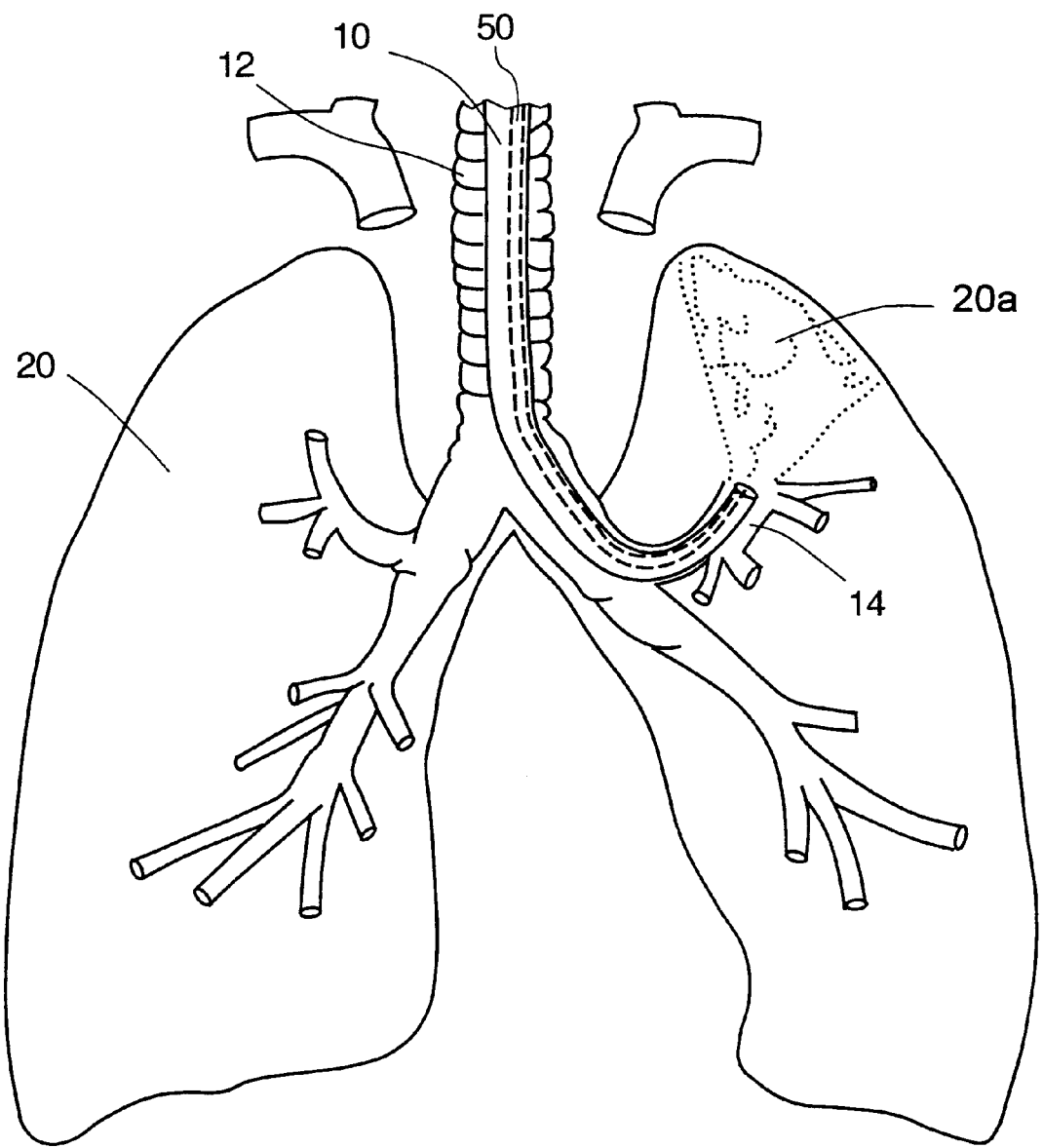
FIG. 1 is a schematic representation of BLVR.

Lung volume can be reduced non-surgically using the devices, compositions, and methods described herein. For example, lung volume can be reduced using a bronchoscope (bronchoscopic lung volume reduction is abbreviated herein as BLVR). Referring to FIG. 1, a flexible bronchoscope 10 is inserted through a patient's trachea 12 to a target region 20a of the lung 20, and a balloon catheter 50 with a distal lumen port 60 (FIG. 2) is inserted through a channel within the bronchoscope. Target region 20a will collapse either when the air passage 14 to target region 20a is occluded or when an anti-surfactant is administered through balloon catheter 50 to target region 20a. Regardless of the cause of collapse, one portion of the collapsed target region will adhere to another when exposed to one or more of the compositions described below. These compositions include substances that can polymerize either spontaneously (e.g., fibrin) or in response to an activator (e.g., fibrinogen). In addition, one or more of the compositions contains a polypeptide growth factor that promotes fibrosis, and may contain an antibiotic to help prevent infection or an additional factor (such as factor XIIIa transglutaminase) to promote polymerization. Following application of the composition(s), the bronchoscope is removed.

Patients who have chronic obstructive pulmonary disease can benefit from BLVR. These patients include, but are not limited to, those who have emphysema, chronic asthma, chronic bronchitis, and brochiectasis. BLVR can also be performed when a patient's lung is damaged by trauma or in the event of a spontaneous pneumothorax.

Identifying and Gaining Access to a Target Region of the Lung

Once a patient is determined to be a candidate for BLVR, the target region 20a of the lung that will be removed can be identified using radiological studies (e.g., chest X-rays) and computed tomography scans. When the procedure is subsequently performed, the patient is anesthetized and intubated, and can be placed on an absorbable gas (e.g. at least 90% oxygen and up to 100% oxygen) for a specified period of time (e.g., approximately 30 minutes). The region(s) of the lung that were first identified radiologically are then identified bronchoscopically.

Suitable bronchoscopes include those manufactured by Pentax, Olympus, and Fujinon, which allow for visualization of an illuminated field. The physician guides bronchoscope 10 into trachea 12 and through the bronchial tree so that the open tip 60 of bronchoscope 10 is positioned at the entrance to target region 20a (i.e., to the region of the lung that will be reduced in volume). Bronchoscope 10 can be guided through progressively narrower branches of the bronchial tree to reach various subsegments of either lung 20. For example, as shown in FIG. 1, the bronchoscope can be guided to a subsegment within the upper lobe of the patient's left lung.

The balloon catheter 50 mentioned above (and described more fully below) is then guided through bronchoscope 10 to target region 20a of lung 20. When catheter 50 is positioned within bronchoscope 10, balloon 58 is inflated so that material passed through the catheter will be contained in regions of the lung distal to the balloon. The targeted region can be lavaged with saline to reduce the amount of surfactant that is naturally present, and a physiologically compatible composition containing an anti-surfactant (i.e., an agent that increases the surface tension of fluids lining the alveoli) is applied to the targeted region of the lung through the catheter. Preferably, the composition is formulated as a solution or suspension and includes fibrin or fibrinogen. An advantage of administering these substances is that they can each act not only as anti-surfactants, but can participate in the adhesive process as well.

Fibrinogen-based Solutions

Fibrinogen can function as an anti-surfactant because it increases the surface tension of fluids lining the alveoli, and it can function as a sealant or adhesive because it can participate in a coagulation cascade in which it is converted to a fibrin monomer that is then polymerized and cross-linked to form a stable mesh. Fibrinogen, which has also been called Factor I, represents about 2–4 g/L of blood plasma protein, and is a monomer that consists of three pairs of disulfide-linked polypeptide chains designated $(A\alpha)_2$, $(B\beta)_2$, and $\gamma_2$. The "A" and "B" chains represent the two small N-terminal peptides and are also known as fibrinopeptides A and B, respectively. The cleavage of fibrinogen by thrombin results in a compound termed fibrin I, and the subsequent cleavage of fibrinopeptide B results in fibrin II. Although these cleavages reduce the molecular weight of fibrinogen only slightly, they nevertheless expose the polymerization sites. In the process of normal clot formation, the cascade is initiated when fibrinogen is exposed to thrombin, and this process can be replicated in the context of lung volume reduction when fibrinogen is exposed to an activator such as thrombin, or an agonist of the thrombin receptor, in an aqueous solution containing calcium (e.g. 1.5 to 5.0 mM calcium).

The fibrinogen-containing composition can include 3–12% fibrinogen and, preferably, includes approximately 10% fibrinogen in saline (e.g., 0.9% saline) or another physiologically acceptable aqueous solution. The volume of anti-surfactant administered will vary, depending on the size of the region of the lung, as estimated from review of computed tomagraphy scanning of the chest. For example, the targeted region can be lavaged with 10–100 mls (e.g., 50 mls) of fibrinogen solution (10 mg/ml). To facilitate lung collapse, the target region can be exposed to (e.g., rinsed or lavaged with) an unpolymerized solution of fibrinogen and then exposed to a second fibrinogen solution that is subsequently polymerized with a fibrinogen activator (e.g., thrombin or a thrombin receptor agonist).

The anti-surfactant can contain fibrinogen that was obtained from the patient before the non-surgical lung reduction procedure commenced (i.e., the anti-surfactant or adhesive composition can include autologous fibrinogen). The use of an autologous substance is preferable because it eliminates the risk that the patient will contract some form of hepatitis (e.g., hepatitis B or non A, non B hepatitis), an acquired immune deficiency syndrome (AIDS), or other blood-transmitted infection. These infections are much more likely to be contracted when the fibrinogen component is extracted from pooled human plasma (see, e.g., Silberstein et al., *Transfusion* 28:319–321, 1988). Human fibrinogen is commercially available through suppliers known to those of skill in the art or may be obtained from blood banks or similar depositories.

Polymerization of fibrinogen-based anti-surfactants can be achieved by adding a fibrinogen activator. These activators are known in the art and include thrombin, batroxobin (such as that from *B. Moojeni, B. Maranhao, B. atrox, B. Ancrod*, or *A. rhodostoma*), and thrombin receptor agonists. When combined, fibrinogen and fibrinogen activators react in a manner similar to the final stages of the natural blood clotting process to form a fibrin matrix. More specifically, polymerization can be achieved by addition of thrombin (e.g., 1–10 units of thrombin per ng of fibrinogen). If desired, 1–5% (e.g., 3%) factor XIIIa transglutaminase can be added to promote cross-linking.

In addition, to promote fibrosis (or scarring) at the site where one region of the collapsed lung adheres to another, one or more of the compositions applied to achieve lung volume reduction (e.g., the composition containing fibrinogen) can contain a polypeptide growth factor. Numerous factors can be included. Platelet-derived growth factor (PDGF) and those in the fibroblast growth factor and transforming growth factory-βfamilies are preferred.

For example, the polypeptide growth factor included in a composition administered to reduce lung volume (e.g., the fibrinogen-, fibrinogen activator-, or fibrin-based compositions described herein) can be basic FGF (bFGF), acidic FGF (aFGF), the hst/Kfgf gene product, FGF-5, FGF-10, or int-2. The nomenclature in the field of polypeptide growth factors is complex, primarily because many factors have been isolated independently by different researchers and, historically, named for the tissue type used as an assay during purification of the factor. This complexity is illustrated by basic FGF, which has been referred to by at least 23 different names (including leukemic growth factor, macrophage growth factor, embryonic kidney-derived angiogenesis factor 2, prostatic growth factor, astroglial growth factor 2, endothelial growth factor, tumor angiogenesis factor, hepatoma growth factor, chondrosarcoma growth factor, cartilage-derived growth factor 1, eye-derived growth factor 1, heparin-binding growth factors class II, myogenic growth factor, human placenta purified factor, uterine-derived growth factor, embryonic carcinoma-derived growth factor, human pituitary growth factor, pituitary-derived chondrocyte growth factor, adipocyte growth factor, prostatic osteoblastic factor, and mammary tumor-derived growth factor). Thus, any factor referred to by one of the aforementioned names is within the scope of the invention.

The compositions can also include "functional polypeptide growth factors," i.e., growth factors that, despite the presence of a mutation (be it a substitution, deletion, or addition of amino acid residues) retain the ability to promote fibrosis in the context of lung volume reduction. Accordingly, alternate molecular forms of polypeptide growth factors (such as the forms of bFGF having molecular weights of 17.8, 22.5, 23.1, and 24.2 kDa) are within the scope of the invention (the higher molecular weight forms being colinear N-terminal extensions of the 17.8 kDa bFGF (Florkiewicz et al., *Proc. Natl. Acad. Sci. USA* 86:3978–3981, 1989)).

It is well within the abilities of one of ordinary skill in the art to determine whether a polypeptide growth factor, regardless of mutations that affect its amino acid content or size, substantially retains the ability to promote fibrosis as would the full length, wild type polypeptide growth factor (i.e., whether a mutant polypeptide promotes fibrosis at least 40%, preferably at least 50%, more preferably at least 70%, and most preferably at least 90% as effectively as the corresponding wild type growth factor). For example, one could examine collagen deposition in cultured fibroblasts following exposure to full-length growth factors and mutant growth factors. A mutant growth factor substantially retains the ability to promote fibrosis when it promotes at least 40%, preferably at least 50%, more preferably at least 70%, and most preferably at least 90% as much collagen deposition as does the corresponding, wild-type factor. The amount of collagen deposition can be measured in numerous ways. For example, collagen expression can be determined by an immunoassay. Alternatively, collagen expression can be determined by extracting collagen from fibroblasts (e.g., cultured fibroblasts or those in the vicinity of the reduced lung tissue) and measuring hydroxyproline.

The polypeptide growth factors useful in the invention can be naturally occurring, synthetic, or recombinant molecules and can consist of a hybrid or chimeric polypeptide with one portion, for example, being bFGF or TGFβ, and a second portion being a distinct polypeptide. These factors can be purified from a biological sample, chemically synthesized, or produced recombinantly by standard techniques (see, e.g., Ausubel et al., *Current Protocols in Molecular Biology*, New York, John Wiley and Sons, 1993; Pouwels et al., *Cloning Vectors: A Laboratory Manual*, 1985, Supp. 1987).

Of course, various fibrosis-promoting growth factors can be used in combination.

One of ordinary skill in the art is well able to determine the dosage of a polypeptide growth factor required to promote fibrosis in the context of BLVR. The dosage required can vary and can range from 1–100 nM.

In addition, any of the compositions or solutions described herein for lung volume reduction (e.g., the fibrinogen-based composition described above) can contain one or more antibiotics (e.g., ampicillin, gentamycin, cefotaxim, nebacetin, penicillin, or sisomicin). The inclusion of antibiotics in therapeutically applied compositions is well known to those of ordinary skill in the art.

Fibrin-based Solutions

Fibrin can also function as an anti-surfactant as well as a sealant or adhesive. However, in contrast to fibrinogen, fibrin can be converted to a polymer without the application of an activator (such as thrombin or factor XIIIa). In fact, fibrin I monomers can spontaneously form a fibrin I polymer that acts as a clot, regardless of whether they are crosslinked and regardless of whether fibrin I is further converted to fibrin II polymer. Without expressing an intention to limit the invention to compounds that function by any particular mechanism, it can be noted that when fibrin I monomers come into contact with a patient's blood, the patient's own thrombin and factor XIII may convert the fibrin I polymer to crosslinked fibrin II polymer.

Any form of fibrin monomer that can be converted to a fibrin polymer can be formulated as a solution and used for lung volume reduction. For example, fibrin-based compositions can contain fibrin I monomers, fibrin II monomers, des BB fibrin monomers, or any mixture or combination thereof. Preferably, the fibrin monomers are not crosslinked.

Fibrin can be obtained from any source so long as it is obtained in a form that can be converted to a fibrin polymer (similarly, non-crosslinked fibrin can be obtained from any source so long as it can be converted to crosslinked fibrin). For example, fibrin can be obtained from the blood of a mammal, such as a human, and is preferably obtained from the patient to whom it will later be administered (i.e., the fibrin is autologous fibrin). Alternatively, fibrin can be obtained from cells that, in culture, secrete fibrinogen.

Fibrin-based compositions can be prepared as described in U.S. Pat. No. 5,739,288 (which is hereby incorporated by referenced in its entirety), and can contain fibrin monomers having a concentration of no less than about 10 mg/ml. For example, the fibrin monomers can be present at concentrations of from about 20 mg/ml to about 200 mg/ml; from about 20 mg/ml to about 100 mg/ml; and from about 25 mg/ml to about 50 mg/ml.

The spontaneous conversion of a fibrin monomer to a fibrin polymer may be facilitated by contacting the fibrin monomer with calcium ions (as found, e.g., in calcium chloride, e.g., a 3–30 mM $CaCl_2$ solution). Except for the first two steps in the intrinsic blood clotting pathway, calcium ions are required to promote the conversion of one coagulation factor to another. Thus, blood will not clot in the absence of calcium ions (but, in a living body, calcium ion concentrations never fall low enough to significantly affect the kinetics of blood clotting; a person would die of muscle tetany before calcium is diminished to that level). Calcium-containing solutions (e.g., sterile 10% $CaCl_2$) can be readily made or purchased from a commercial supplier.

The fibrin-based compositions described here can also include one or more polypeptide growth factors that promote fibrosis (or scarring) at the site where one region of the collapsed lung adheres to another. Numerous factors can be included and those in the fibroblast growth factor and transforming growth factor-β families are preferred. The polypeptide growth factors suitable for inclusion with fibrin-based compositions include all of those (described above) that are suitable for inclusion with fibrinogen-based compositions.

Application of Fibrin- and Fibrinogen-based Compositions following Lung Collapse While a targeted region of the lung can be collapsed by exposure to one of the substances described above, these substances can also be applied to adhere one region of the lung to another (and to promote fibrosis) when the collapse has been induced by other means. For example, the substances described above can be applied after the lung collapses from blockage of airflow into or out of the targeted region. Such blockage can be readily induced by, for example, inserting a bronchoscope into the trachea of an anesthetized patient, inserting a balloon catheter through the bronchoscope, and inflating the balloon so that little or no air passes into the targeted region of the lung. Collapse of the occluded region after the lung is filled with absorbable gas would occur over approximately 5–15 minutes, depending on the size of the region occluded. Alternatively, the target region could be Alternatively, a fibrinogen- or fibrin-based solution can be applied after the lung is exposed to another type of anti-surfactant (e.g., a non-toxic detergent).

A Catheter for Application of Material to the Lung

Referring to FIG. 2a, any of the substances described above can be administered to the lung by a balloon catheter 50 having multiple ports 52 through which materials (such as solutions or suspensions) or gases (such as air) can be injected via a corresponding number of lumens.

The ports of catheter 50 are arranged as follows. A first port 54 having a proximal end 54a adapted for connection with a gas supply (e.g., a leur-lock syringe containing air) communicates with internal lumen 56 of catheter 50, which terminates within inflatable balloon 58 near distal tip 60 of catheter 50. A second port 64 having a proximal end 64a adapted for connection with a source of one or more materials (e.g., medication cartridge 80, described below) communicates with internal lumen 66, which terminates at open distal tip 60 of catheter 50. A third port 74 having a proximal end 74a adapted for connection with a source of one or more materials (e.g., medication cartridge 80) communicates with internal lumen 76, which also terminates at open distal tip 60 of catheter 50.

Thus, gas injected through port 54 travels through internal lumen 56 to inflate balloon 58, and material injected through port 64 and/or port 74 travels through internal lumens 66 and 76, respectively, to distal tip 60 of catheter 50. Upon reaching distal tip 60 of catheter 50, materials previously separated within lumens 66 and 76 would mix together.

Referring to FIG. 2b, internal lumen 54, internal lumen 64, and internal lumen 74 are shown in a cross-sectional view of shaft 51 of catheter 50. In another embodiment, lumens 66 and 76 can differ in size, with the diameter of the lumen through which the fibrinogen-based solution is applied being approximately twice as great as the diameter of the lumen through which the solution containing the fibrinogen activator is applied.

Figure 2C:
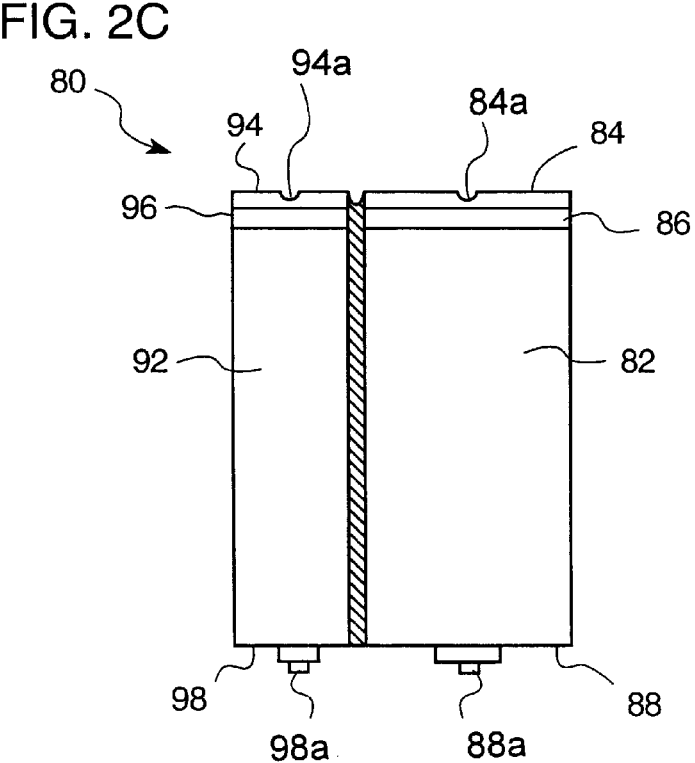

Referring to FIG. 2c, cartridge 80 can be attached to catheter 50 to inject material via ports 64, 74 and lumens 66, 76. Cartridge 80 includes a first chamber 82 and a second chamber 92, either or both of which can contain material useful in BLVR (e.g., chamber 82 can contain a mixture of fibrinogen, TGF-β, and gentamycin, and chamber 92 can contain thrombin in a calcium-buffered solution). Material within cartridge 80 can be administered to the lung by way of catheter 20, as follows. Upper wall 84 of chamber 82 includes orifice 84a, through which pressure can be applied to depress plunger 86. Depression of plunger 86 forces material within chamber 82 toward lower wall 88 of chamber 82, through opening 88a, and, when cartridge 80 is attached to catheter 50, into port 64 of catheter 50. Similarly, upper wall 94 of chamber 92 includes orifice 94a, through which pressure can be applied to depress plunger 96. Depression of plunger 96 forces material within chamber 92 toward lower wall 98 of chamber 92, through opening 98a, and, when cartridge 80 is attached to catheter 50, into port 74 of catheter 50.

Figure 2D:
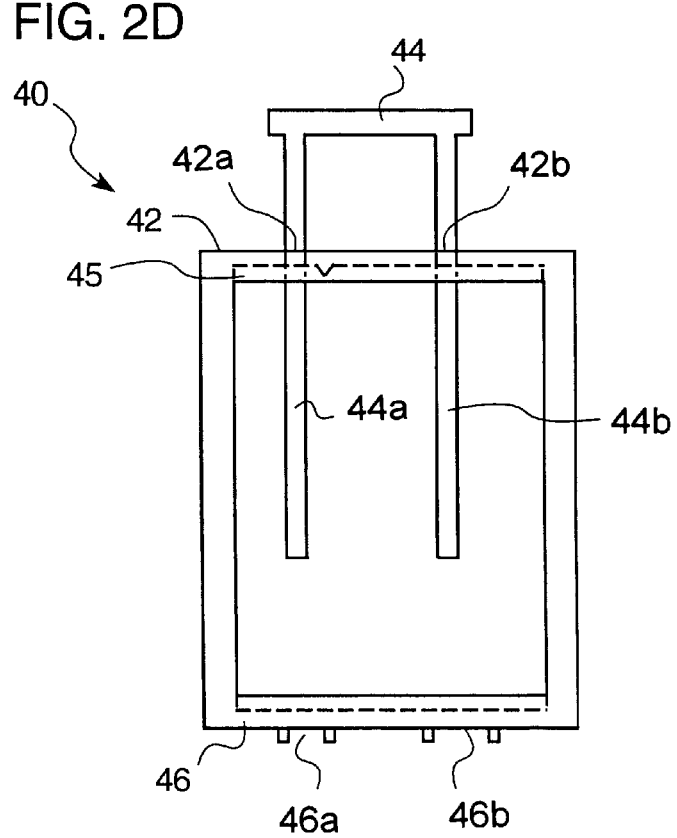
FIG. 2d illustrates an injector that can be used to expel material from the cartridge illustrated in FIG. 2c.
Figure 3B:
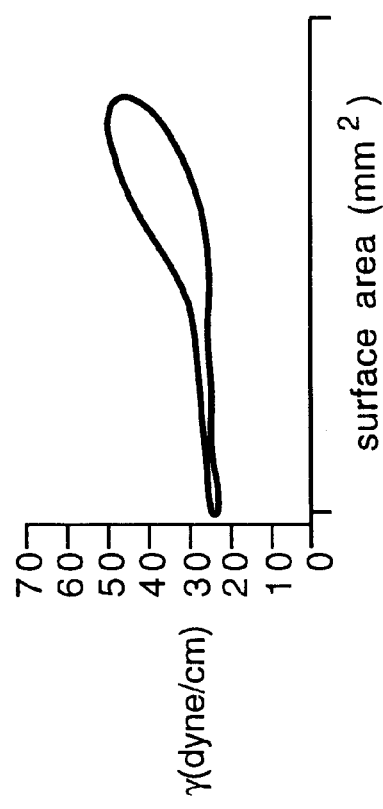
FIGS. 3a and 3b are graphs depicting the surface tension vs. surface area of surfactant films from a control guinea pig (FIG. 3a) and a guinea pig exposed to LPS (FIG. 3b).
Figure 3A:
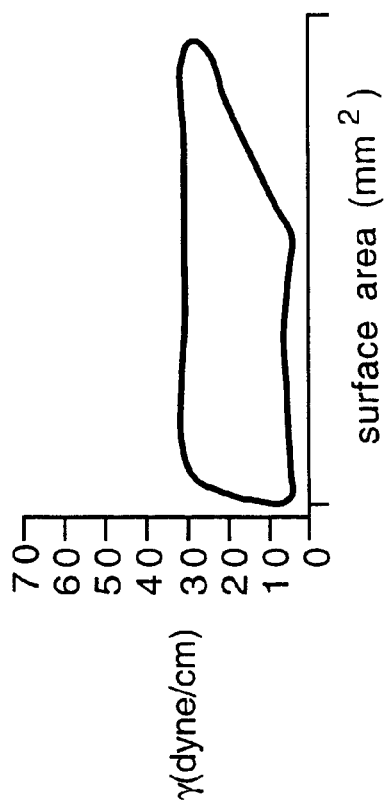
Figure 4B:
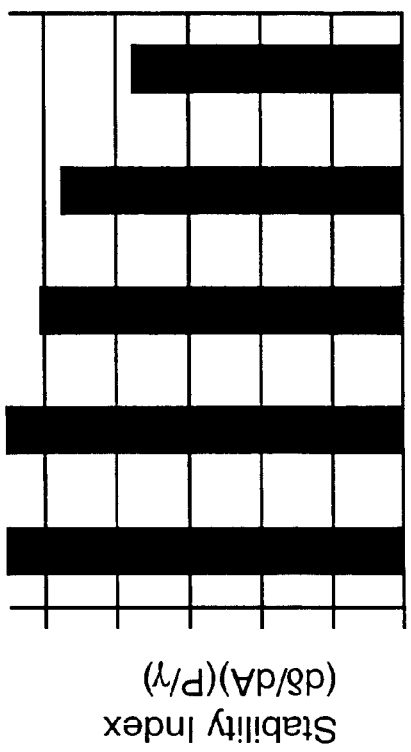
FIGS. 4a and 4b are bar graphs depicting the surface film stability parameter (Gy/dA)l(A/y) as a function of protein/lipid concentration for fibrinogen and albumin surfactant mixtures.
Figure 4A:
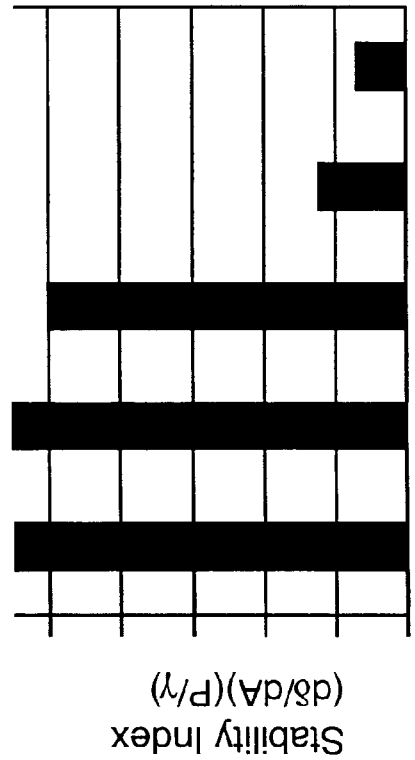

Referring to FIG. 2d, to aid the transfer of material from cartridge 80 to catheter 50, cartridge 80 can be placed within recess 45 of a frame-shaped injector 40. Injector 40 includes upper wall 42, having orifices 42a and 42b, through which arm 44 is inserted. Prong 44a of arm 44 enters injector 40 through orifice 42a and prong 44b of arm 44 enters injector 40 through orifice 42b. When cartridge 80 is placed within injector 40 and arm 44 is depressed, prongs 44a and 44b are forced against plungers 86 and 96, respectively, thereby extruding materials in chambers 82 and 92 through openings 88a and 98a, respectively, of cartridge 80 and openings 46a and 46b, respectively, of lower wall 46 of injector 40.

FIG. 2e illustrates catheter 50 assembled with cartridge 80, injector 40, and a leur-lock, air-filled syringe 30.

The preferred methods, materials, and examples that will now be described are illustrative only and are not intended to be limiting; materials and methods similar or equivalent to those described herein can be used in the practice or testing of the invention.

EXAMPLE 1

BLVR in an Isolated Calf Lung

Isolated calf lungs are excellent models for BLVR because they are easy to work with and anatomically similar to human lungs. Calf lungs having 4–5 liters total lung capacity were purchased from Arena and Sons' Slaughter House (Hopkinton, Mass.) and delivered on ice to the laboratory within 3 hours of procurement. The lungs were tracheally cannulated with a #22 tubing connector and suspended from a ring clamp with the diaphragmatic surface resting in a large Teflon dish containing 2–3 mm of phosphate buffered saline (PBS). The visceral pleural surface was kept moist by spraying it with a mist of 0.15 M NaCl at regular intervals. Pleural leaks were identified by the appearance of bubbles on the pleural surface and by assessing the lungs' ability to hold a constant pressure of 20 cm $H_2O$ inflation pressure. Leaks were sealed by autologous buttress plication. Any adversely affected sections of the lungs were rolled up and stapled in a manner similar to that used in LVRS in humans (Swanson et al., *J. Am. Coll. Surg.* 185:25–32, 1997).

Absolute lung volumes were measured by gas dilution using nitrogen as the tracer gas (Conrad et al., *Pulmonary Function Testing—Principles and Practice*, Churchill Livingstone Publishers, New York, N.Y., 1984). Measurements were performed at 0 cm $H_2O$ transpulmonary pressure as follows. A three liter syringe was filled with 1.5 liters of 100% oxygen from a reservoir bag. The isolated lung, containing an unknown volume of room air (79% nitrogen) was then connected in-line with the syringe containing 0% nitrogen via a three way valve. The gas was mixed well by depressing the plunger of the syringe 60–100 times, and the equilibrium concentration of nitrogen was then determined using a nitrogen meter (Medtronics, Model 830 Nitrogen meter). The unknown starting lung volume of room air was then calculated according to the following conservation of mass equation:

$$VL = \{F_{N2f}/(0.79 - F_{N2f})\} \cdot 1.5 \text{ L}$$

where $F_{N2f}$ is the fraction of nitrogen measured at steady state following mixing with 1.5 liters of oxygen from the syringe. This measurement defines the single absolute lung volume that is required to characterize static lung mechanics.

Quasi-static deflation pressure volume curves (QSPVC) were then recorded during step-wise deflation from 20 cm $H_2O$ to 0 cm $H_2O$ transpulmonary pressure as follows.

Lungs were filled with air to 20 cm $H_2O$ transpulmonary pressure, and the trachea was then occluded manually. Transpulmonary pressure was recorded using a 50 cm $H_2O$ pressure transducer positioned at the airway opening. Expired lung volume was measured using a pneumotachograph (Hans Rudolf Inc, Kansas City, Mo.) connected in series with the tracheal cannula. Pressure as a function of expired lung volume (referenced to the starting volume at 20 cm $H_2O$) was determined by intermittently occluding the trachea. Occlusions were maintained long enough to allow for equilibration of tracheal and alveolar pressures (no change in tracheal pressure over three seconds). By combining the single absolute lung volume measurement made by nitrogen dilution at zero transpulmonary pressure with QSPVC data, complete static recoil pressure volume relationships were determined. These relationships can be described as an exponential function according to the equation of Salazar et al. (*J. Appl. Physiol.* 19:97–104, 1964):

$$V(P) = V_{max} - A e^{-kP}$$

where V is lung volume as a function of transpulmonary pressure; P is transpulmonary pressure; $V_{max}$ is the extrapolated lung volume at infinite pressure (approximately equal to TLC); A is the difference between $V_{max}$ and the volume of gas trapped within the lung at zero transpulmonary pressure (approximately equal to vital capacity); and k is the shape factor which describes the curvature of the exponential relationship between pressure and volume independent of the absolute volume of the lung. The parameters $V_{max}$, A, and k were determined from a best fit linear regression analysis, and recoil pressure at total lung capacity (PTLC) determined by direct measurement.

It is useful to express the pressure volume relationship in terms of the parameters described above because each parameter is known to change in a characteristic fashion in emphysema. Thus, one can anticipate specific changes following interventions designed to either produce emphysema (e.g. papain exposure in the animal model) or correct the abnormalities of emphysema (e.g., volume reduction; see Gibson et al., *Am. Rev. Resp. Dis.* 120:799–811, 1979). For example, $V_{max}$ increases in emphysema due to lung hyperexpansion (this reflects an increase in total lung capacity); k, the shape factor, also increases due to a decrease in the slope of the pressure volume relationship at low lung volumes; and A, the difference between maximal lung volume and trapped lung gas at zero transpulmonary pressure, decreases because trapped gas increases out of proportion to total lung capacity. These abnormalities will improve following effective lung volume reduction.

Following completion of lung volume and QSPVC measurements, lung function was assessed during simulated tidal ventilation. A solenoid driven computer controlled pneumatic ventilator was developed for this purpose. This device allows for measurements of lung resistance and dynamic elastance during oscillatory ventilation, while monitoring and maintaining a constant user specified mean airway pressure. Flow (V) into and out of the lung was measured using a pneumotachometer, volume (V) was determined by integration of the flow signal, and transpulmonary pressure (Ptp) was recorded as airway opening pressure referenced to atmospheric pressure.

The flow pattern chosen for measuring lung function was an optimal ventilation waveform (OVW) pattern developed by Lutchen et al. (*J. Appl. Physiol.* 75:478–488, 1993). This pattern represents the sum of a series of sinusoids selected to provide tidal ventilation while simultaneously minimizing signal distortion due to nonlinear effects of the respiratory system (Suki et al., *J. Appl. Physiol.* 79(2):660–671, 1995). Lung function was assessed by determining impedance, the ratio of pressure to flow in the frequency domain, by Fourier analysis. The real and imaginary parts of the impedance signal represent lung resistance and lung reactance, respectively. Lung resistance is, in turn, equal to the sum of tissue resistance ($R_{ti}$) and airway resistance ($R_{aw}$), while lung reactance is determined by a combination of elastance and gas inertance effects. Thus, in contrast to standard sinusoidal or constant flow ventilation, OVW measurements allow for the determination of airway resistance, tissue resistance, and dynamic elastance (Edyn) over a range of frequencies from a single measurement. This detailed information is useful for several reasons. Volume reduction is a procedure which has the potential for affecting all three of these lung function parameters. In emphysema, volume reduction should reduce $R_{aw}$ by improving airway tethering, thereby stretching airways open. Because volume reduction increases tissue stretching, however, it will tend to increase tissue resistance. Total lung resistance, the sum of $R_{aw}$ and $R_{ti}$, can therefore be variably affected depending upon how LVR individually affects $R_{aw}$ and $R_{ti}$. In most instances, there should be some optimal range of tissue resection that can produce a substantial decrease in Raw, but only a small increase in $R_{ti}$. The OVW approach helps define this optimum. An additional benefit of the OVW approach is that it provides a non-invasive assessment of lung function heterogeneity. The presence of heterogeneity, which physiologically produces a positive frequency dependence in lung elastance, can be detected by the OVW technique (Lutchen et al., *J. Appl. Physiol.* 75:478–488, 1993). In the normal lung, elastance is relatively frequency independent since most regions have similar mechanical properties leading to uniform gas flow distribution. In a diseased lung, regional differences in impedance to gas flow exist, and elastance increases with increasing frequency. In emphysema, frequency dependence of elastance is a characteristic finding and reflects regional differences in disease severity. A successful volume reduction targeted at a diseased region should reduce heterogeneity and frequency dependence of elastance. Thus, reduction in frequency dependence of elastance can be used as an index of a successful BLVR procedure, and can be readily determined from the OVW measurement. It is expected that any measurement made immediately following BLVR would underestimate the improvement that will become evident once a mature scar has formed. At that time, a 25–50% improvement in expiratory flow rates could be observed. Thus, any fibrin- or fibrinogen-based composition described above is within the scope of the invention if, when applied according to a BLVR procedure, it produces a 25–50% improvement in expiratory flow rates.

Measurements of lung volumes, quasi-static pressure volume relationships, and lung resistance and dynamic elastance as functions of frequency were determined in three isolated, naive calf lungs before and after plication volume reduction. Dynamic recordings were made at 9–10 cm $H_2O$ mean transpulmonary distending pressure (PEEP=5 cm $H_2O$) via the OVW technique at tidal volumes of 10% of measured $V_{max}$. Small leaks present following plication were sealed with cyanoacrylate glue. The estimated time between initial and post-reduction recordings was between 60 and 90 minutes.

Pre- and post-volume reduction lung physiology recordings in the isolated calf lung are summarized below in Table 1.

TABLE 1

Static and Dynamic Lung Mechanics Measured in Isolated Calf Lungs Before and following Plication Lung Volume Reduction

| Lung | Raw (0.2 Hz) (cm H2O/L/sec) | | Rti (0.2 Hz) (cm H2O/L/sec) | | (cm H2O/L) | | Edyn Vmax (liters) | |
|---|---|---|---|---|---|---|---|---|
| | pre | post | pre | post | pre | post | pre | post |
| 1 | 0.42 | 0.48 | 1.31 | 1.30 | 18.1 | 22.2 | 4.4 | 3.8 |
| 2 | 1.10 | 0.85 | 1.60 | 2.36 | 26.3 | 29.4 | 3.5 | 3.1 |
| 3 | 0.82 | 0.88 | 3.08 | 2.92 | 40.1 | 36.2 | 2.9 | 2.7 |
| Mean | 0.78 | 0.74 | 2.00 | 2.19 | 28.2 | 29.2 | 3.6 | 3.2 |
| Std dev | 0.34 | 0.22 | 0.94 | 0.82 | 11.1 | 7.0 | 0.75 | 0.56 |

These results indicate that, in normal calf lungs, a 10–15% volume reduction (mean 11.1%) produces no significant change in dynamic elastance, airway resistance, or tissue resistance. They further demonstrate that detailed function can be measured in isolated lungs using the measurement system described herein and that successful plication volume reduction can be performed on isolated lungs, which serve as controls for BLVR experiments.

EXAMPLE 2

Fibrinogen-based Anti-surfactants

Mechanical equilibrium across the alveoli and small airways is determined by a balance between distending forces, which are exerted by transpulmonary gas pressure pushing outward, and recoil forces, which are exerted by parenchymal tissue structures and the surface film lining the air liquid interface, both of which pull inward and act to promote lung collapse. For the alveoli and small airways to remain patent during normal breathing, destabilizing force perturbations must be balanced by intrinsic stabilizing forces. The tendency for the lung to resist destabilization and atelectasis can be expressed in terms of two biomechanical properties: the bulk modulus (K) and the shear modulus (p). The value of K is proportional to the lung's ability to resist distortion resulting from forces directed perpendicular (or normal) to a region of tissue (Martinez et al., *Am. J. Resp. Crit. Care Med.* 155:1984–1990, 1997), and the value of p is proportional to the lung's ability to resist distortion resulting from shearing forces imposed on a region of tissue (Stamenovic, *Physiol Rev.* 70:1117–1134, 1990). The larger the values of K and p, the greater the tendency of intrinsic forces within the lung to resist external perturbations and atelectasis. Conversely, any factors which lower K and p tend to promote alveolar instability and collapse resulting in atelectasis. The values of the shear and bulk moduli depend on both tissue and surface film properties and can be quantitatively expressed as (Stamenovic, *Physiol Rev.* 70:1117–1134, 1990):

$$K = 1/3\{(B-2) \cdot P_{tis}\} + 1/3\{(3b-1) \cdot P_\gamma\}$$

$$\mu = (0.4 + 0.1B) \cdot P_{tis} + 0.4 \cdot P_\gamma$$

where B is a normalized elastance for the tissue components (elastin, collagen, and interstitial cells) of the lung; $P_{tis}$ is the recoil pressure of tissue components in the absence of surface film recoil; b is a normalized elastance for the surface film at the air-liquid interface; and $P_\gamma$ is the recoil pressure of the surface film in the absence of tissue recoil.

In the healthy lung, surface forces account for two-thirds to three-quarters of lung recoil, and thus the contribution of the $P_\gamma$ terms to the bulk and shear moduli are primarily responsible for determining stability. In emphysema, where tissue elements are destroyed and exert less recoil, the role of surface forces in determining parenchymal stability is of even greater importance.

The primary goal of these experiments was to develop a biocompatible reagent that could be instilled bronchoscopically to produce site-specific alterations in surface film behavior so as to promote alveolar instability and collapse (i.e., to develop an anti-surfactant). This can be achieved if the liquid film lining the alveoli and small airways undergoes a reduction in bulk and or shear moduli as a result of chemical modification. In essence, this requires a solution that can alter the surface tension lowering properties of native lung surfactant without producing other undesired effects. From a biomedical perspective, the characteristic parameter of the surface film which can be most readily affected by such external chemical manipulation is the dimensionless film elastance prameter, b, which is equal to $b' \cdot (\delta\gamma/\delta A)(V/A)$, where $\gamma$ is the surface tension of the film; A is the area of the surface over which the film is spread, and b' is a proportionality constant that varies depending upon the geometry of the region in question. For normal lung surfactant $(\delta\gamma/\delta A)$ $(V/A)$ (define as $b^*=b/b'$) assumes values of approximately 100–110. As b decreases (i.e. $\delta\gamma/\delta A$ becomes smaller or $\gamma$ becomes larger) within a given region, the local surface forces act more to destabilize rather than stabilize the alveoli. Thus, films with low elastance (relatively flat surface tension versus surface area profiles) or elevated surface tensions tend to promote destabilization.

Examples of stable and unstable surface films displaying these patterns of behavior are shown in FIGS. 3*a* and 3*b*. FIG. 3*a* shows a surface tension-surface area profile measured by pulsating bubble surfactometry (PBS) for normal surfactant at 1 mg/ml concentration isolated from the lung of a normal guinea pig. It demonstrates both a positive film elastance ($\delta\gamma/\delta A>0$) and low minimum surface tension ($\gamma_{min}<3$ dyne/cm). Such a film possesses positive values for the biophysical parameters b, K, and p and thus would promote stability in vivo. In contrast to normal surfactant, a sample isolated from an animal with acute lung injury and atelectasis following endotoxin infusion shows nearly zero elastance and an elevated minimum surface tension (FIG. 3*b*). This film has a bulk modulus of less than zero, and thus would promote alveolar instability and collapse. While these biophysical features are detrimental in the setting of acute lung injury, the ability to impose such features on a film in a controlled fashion is obviously desirable in conducting the present experiments.

Because the dysfunction observed above occurs in vivo, characterizing the biochemical changes in surfactant that accompany this dysfunction will suggest biocompatible reagents that are useful in BLVR. Surfactant samples isolated from animals treated with lipopolysaccharide (LPS) are in large part dysfunctional as a result of alterations in interfacial properties due to mixing with serum proteins, which have entered the alveolar compartment across the damaged basement membrane (Kennedy et al., *Exp. Lung Res.* 23:171–189, 1997).

To determine whether fibrinogen solutions could be added to native surfactant to produce significant surface film dysfunction, calf surfactant was isolated by lavage and centrifugation from calf lungs provided fresh from a local slaughter house. Bovine fibrinogen was purchased commercially (Sigma Chemical Co., St. Louis, Mo.). Stock solutions of each reagent were prepared in normal saline, and mixed at mg ratios (fibrinogen to surfactant phospholipid content) of 0.1:1, 0.5:1, 1.0:1, 5.0:1, and 10.0:1. The results were compared to mixtures of calf lung surfactant and bovine serum albumin.

Surface tension recordings were made by pulsating bubble surfactometry at 37° C., oscillation frequency of 20 cycles/min, and area amplitude ratio of 72%, continuously, for 5 minutes (Enhorning, *J. Appl. Physiol.* 43:198–203, 1977). Based on measurements of surface tension versus surface area, values for the film stability parameter, $(\delta\gamma/\delta A)/(A/\gamma)$, were determined and expressed as a function of protein to phospholipid concentration ratio. The results are summarized in FIGS. 4*a* and 4*b*. These results suggest that fibrinogen is a more potent inhibitor of surfactant function than albumin and is able to generate marked surface film instability (expressed in terms of the film stability criteria b*, at protein to lipid concentration ratios of less than 5:1). These concentration ratios are readily achievable in vivo using concentrated fibrinogen solutions.

To test fibrinogen solutions in isolated calf lungs, stock solutions of bovine fibrinogen (Sigma Chemical, St. Louis, Mo.) in 5 mM Tris-HCl (pH 7.4) and partially purified thrombin in 5 mM Tris-HCl containing 5 mM $CaCl_2$, were prepared. Mixing studies demonstrated that ratios of fibrinogen to thrombin of between 10:1 to 3:1 (mg:mg) resulted in polymerization within 3–5 minutes. A ratio of 10:1 was selected for whole lung testing. Isolated calf lungs were cannulated, suspended from a ring clamp, and subjected to baseline lung volume and QSPVC measurements as described above. At zero transpulmonary pressure under direct bronchoscopic visualization, the bronchoscope was wedged in a distal subsegment approximately 5 mm in diameter. The subtended surface was then lavaged with 50 mls of fibrinogen solution (10 mg/ml) injected through a P-240 polypropylene catheter passed through the suction port. The fibrinogen solution was stained with several drops of concentrated Evans blue to allow for ready identification of the target region. The catheter was then removed, and suction was applied directly through the suction port of the scope to complete the rinsing procedure. Lavage return averaged 28 mls in the 4 lavage procedures performed (56% return). The catheter was then replaced into the affected region and 4 mls of thrombin in calcium containing buffer were instilled. A second lavage and polymerization procedure was then performed in a different subsegment. Repeat lung volumes and quasi-static pressure volume profiles were then recorded. The results are summarized in Table 2.

TABLE 2

Effect of Fibrinogen Instillation and Polymerization on Lung Volumes

| | Pre-instillation Volume (L) | Post-instillation volume (L) |
|---|---|---|
| Lung #1 | 3.4 | 2.9 |
| Lung #2 | 3.1 | 2.8 |

These data indicate that even without the addition of factor XIIIa to promote clot stabilization, reductions in lung volume were achieved that significantly exceeded the retained volume of polymerizing solution, indicating that sustained collapse had been achieved.

EXAMPLE 3

Fibrinogen- and Fibrin-based Solutions Containing Growth Factors

Any potential anti-surfactant can be evaluated in the assay described above, which demonstrated that fibrinogen solutions possess many of the features desired for an anti-surfactant. In addition to the fibrinogen solution described above, one can use solutions that impart additional characteristics to compositions that can be used to perform BLVR in vivo. For example, the fibrinogen solution can be modified to support fibroblast growth and to serve as a reservoir for antibiotics. Any modified fibrinogen solution can be used in conjunction with factors that promote fibrosis so long as the fibrinogen maintains the ability to inhibit surfactant and undergo polymerization.

Basic fibroblast growth factor (bFGF) and/or transforming growth factor-beta (TGFβ) can be added to solutions of fibrinogen, as can an antibiotic mixture of ampicillin and gentamicin, which can be added in amounts sufficient to exceed the minimal inhibitory concentration for most bacteria.

In vitro studies can be conducted to determine appropriate concentrations of factor XIIIa relative to fibrinogen and thrombin, and assess how growth factors and antibiotics affect this final cross-linking step. The surface tension of surfactant fibrinogen mixtures can be measured in vitro using a commercially available pulsating bubble surfactometer (PBS) unit. Measurements of surface tension as a function of surface area can be performed at 37° C., oscillation frequency of 20 cycles/min, and a relative surface area change that approximates that of tidal breathing ($\delta A/A= 20$–$30\%$).

Equilibrium and dynamic surface tension recordings can also be made. Recordings can be performed at 30 seconds, 5 minutes, and 15 minutes to ensure that any surface film dysfunction observed initially is sustained throughout the measurement period. The stability of each film preparation can be expressed in terms of b*, the dimensionless surface film elastance ($\delta\gamma T/dA \cdot A/\delta$) described above normalized to b* values measured for native calf lung surfactant. Mixtures displaying normalized b* values of <0.2 would be acceptable for additional testing as anti-surfactants.

Calf lung surfactant can be isolated from whole calf lungs as previously described (Kennedy et al., *Exp. Lung Res.* 23:171–189, 1997), and bovine fibrinogen, bFGF, factor XIIIa transglutaminase, and TGFβ can be purchased from commercial suppliers (e.g., Sigma Chemical Co., St. Louis, Mo.).

Surface tension behavior for samples with fibrinogen:surfactant ratios ranging between 0.01 to 10 (mg protein:mg lipid) can be prepared in phosphate buffered saline (0.15 M, pH 7.3). The following six mixtures were chosen because they are representative of mixtures that may be useful in vivo, and they contain components of partially polymerized fibrin that may exist within the lung during the process of polymerization. Thus, they represent the behavior of partially polymerized mixtures in vivo and can be assessed to determine whether the ability of fibrinogen to inhibit surfactant function changes as it undergoes polymerization.

Test mixtures will include surfactant (at 1 mg/ml) with appropriate amounts of: (1) fibrin monomer alone; (2) fibrin monomer with FGF and TGFβ; (3) fibrin monomer with FGF, TGFβ, ampicillin, and gentamicin; (4) fibrinogen with FGF and TGFβ; (5) fibrinogen with FGF, TGFβ, ampicillin, and gentamicin; and (6) fibrinogen with FGF, TGFβ, ampicillin, gentamicin, and thrombin. Recordings will be discontinued for the samples that undergo polymerization during surface film measurements (thereby making measurements of γ vs A impossible), and the time to polymerization will be noted.

Clot stability can be tested in vitro on solutions of surfactant-fibrinogen mixtures containing antibiotics and growth factors which demonstrate sustained abnormalities in interfacial properties by PBS measurements. Factor XIIIa can be added to these samples to promote clot cross-linking. Clot stability at several concentrations of added factor XIIIa can be examined by assaying for clot dissolution in 8 M urea (plasma clot lysis time).

Both fibrin monomers and fibrinogen should cause significant alterations in surface film behavior (normalized b* values <0.2) at protein:phospholipid ratios >4). Moreover, the addition of thrombin, antibiotics, or growth factors should not markedly alter the ability of fibrin compounds to inhibit surfactant function at the concentrations required for these reagents to function in vivo. If these additives do markedly alter the biophysics of the interaction between surfactant and fibrinogen/fibrin, alternative reagents (or alternative reagent concentrations), can readily be considered.

A stable long term state of atelectasis with scarring within the targeted region is necessary to prevent subsequent partial or complete re-expansion following BLVR. This state can be achieved by using a biopolymer that promotes ingrowth of fibroblasts from adjacent regions within the lung and causes deposition of extracellular matrix (ECM) components. The procedures described below can be used to examine the ability of fibrin polymers containing varying concentrations of growth factors to stimulate fibroblast ingrowth. More specifically, they can be used to examine the ability of polymers with varying concentrations of growth factors to promote both initial cell attachment and subsequent growth.

Cell culture plates are coated with a mixture of fibrinogen, antibiotics, FGF (both with and without TGFβ), and the mixture is polymerized by addition of a small amount of thrombin. The plates are then washed with sterile Eagle's minimal essential medium to remove excess reagents and thrombin, and sterilized by overnight exposure to ultraviolet irradiation. Six types of plates are examined initially: the first and second are coated with fibrin polymer, antibiotics, and FGF at either a low or high concentration; the third and fourth are coated with fibrin polymer, antibiotics, and TGFβ at either low or high concentration; and the fifth and six are coated in similar fashion but contain both growth factors at either low or high concentrations.

Strain IMR-90 (human diploid fibroblasts available from the American Type Culture Collection, Manassas, Va.) are cultured in minimal essential tissue culture medium containing 10% fetal calf serum. Cells are brought to 80% confluence following initial plating, then harvested and passed twice in serum free media (MCDB-104, Gibco 82-5006EA, Grand Island, N.Y.). Established cultures are then sub-cultured onto coated 6-well plates at an initial density of $10^4$ cells/ml. Attachment efficiency (AE) for each coating mixture is assessed at 4 hours following plating by removing excess media, rinsing the wells in culture free media, and fixing each well with 70% histologic grade ethanol (Fisher Scientific, Pittsburgh, Pa.). Wells are stained with Geimsa, and the average number of cells attached per high power field (hpf) is determined by light microscopy. Twenty fields per well will be assessed in a blind study. Six wells per coating will be averaged to determine final counts, and the results will be compared to those of control samples plated on tissue culture plastic. Attachment efficiency will be expressed as an index (AEI) equal to the ratio of the number cells/hpf in experimental samples to the number of cells/hpf in control samples. Cell growth on each of the six biopolymer mixtures is assessed by determining the total number of cells present at 48 hours following plating. Cell growth is expressed in terms of a growth efficiency index (GEI) equal to the total number of cells at 48 hours for each sample normalized to the total number of cells at 48 hours of growth on tissue culture plastic. Cell harvesting and counting is performed by removing the media from each well, and rinsing with calcium/magnesium free Hank's solution. The media will be saved for cell re-suspension. One ml of 0.2% trypsin solution is added to each well, and the cells are incubated for 2 minutes. Trypsin is then removed, and the adherent cells washed from the plate using the previously harvested media, which acts to inhibit further trypsin activity. The extent of residual cell adhesion is assessed by direct visualization using an inverted microscope. Residual adherent cells are removed by a second trypsin wash and total cell counts are obtained using a hemocytometer.

Cell attachment to a fibrin polymer should be equivalent to, or better than, that observed on tissue culture plastic. If cell attachment is poor using fibrin alone, the fibrinogen will be mixed with 3–5% fibronectin and polymerized. Fibronectin has fibrin binding sites at both its amino and carboxyl termini, with a central cell binding domain which is recognized by most adherent cells expressing β1 integrins. Addition of fibrinogen should result in improved cell adhesion.

GEI should also be increased in preparations containing bFGF at low and high concentrations, but may be decreased in preparations containing TGFβ because of the suppressant effects of TGFβ on cell proliferation. However, it should be possible to overcome any suppressant effects observed using TGFβ by using a combination of bFGF and TGFβ. This combination has the potential to promote both cellular ingrowth and increase collagen and fibronectin deposition with scar formation. If bFGF is not able to overcome the anti-proliferative effects of TGFβ, platelet derived growth factor (PDGF) may be used.

EXAMPLE 4

A Sheep Model for Emphysema

Work in live animals can help establish the effectiveness, safety, and durability of BLVR. The sheep model of emphysema described here displays many of the physiological, histological, and radiographic features of emphysema. In preliminary studies, six adult ewes (weighing 27–41 kg) were treated with inhaled nebulized Papain, a commercially available mixture of elastase and collagenase, administered via a muzzle-mask using two high flow nebulizer systems connected in parallel. The system generates particles 1–5 microns in diameter. Each animal received 7,000 units of enzyme in saline over a 90 minute period at 0.3 ml/min. Approximately 30–40% of the total dose administered in this fashion was deposited at the alveolar level. One animal, which received saline according to a similar protocol, served as control.

All animals underwent detailed measurements of lung function before, and at monthly intervals after, inhalation treatments. The post-treatment assessment was continued for 3 months. Recordings were made following administration of anesthesia during controlled ventilation. Transpulmonary pressure was recorded using a pressure transducer, which recorded the pressure difference between the airway opening and the intrathoracic pressure measured using an esophageal balloon. Flow at the mouth was measured using a pneumotachograph attached to the proximal end of the endotracheal tube. Measurements of lung resistance, static lung compliance, and dynamic lung compliance were performed. After 3 months, all animals were sacrificed, and lung sections were prepared for histopathological evaluation.

The results of static and dynamic lung compliance measured prior to exposure to Papain and at 3 months following Papain treatment, are summarized in FIGS. 5a and 5b. Static lung compliance increased significantly from 0.13±0.02 to 0.18±0.03 L/cm $H_2O$ (p=0.012, n=6), indicating disease heterogeneity and gas trapping.

Figure 6B:
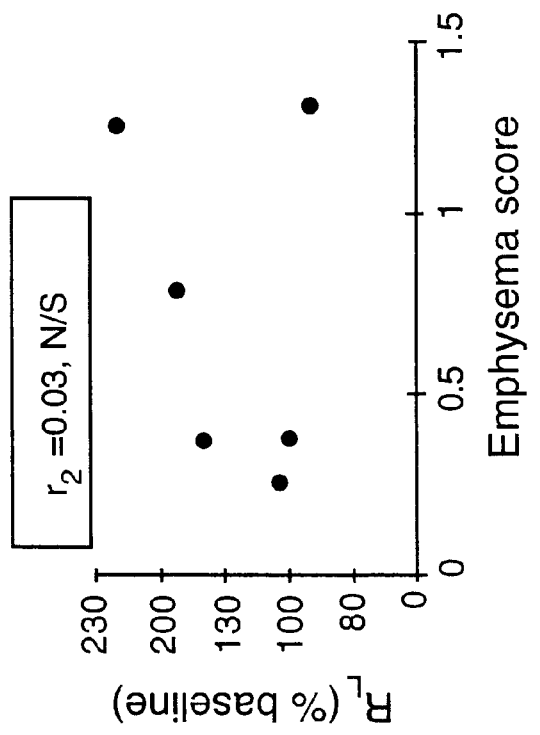
FIGS. 6a and 6b are graphs plotting the relationship between physiology (Cdyn, as a % baseline, is shown in FIG. 6a and $R_L$, also as a % baseline, is shown in FIG. 6b) and emphysema severity score.
Figure 6A:
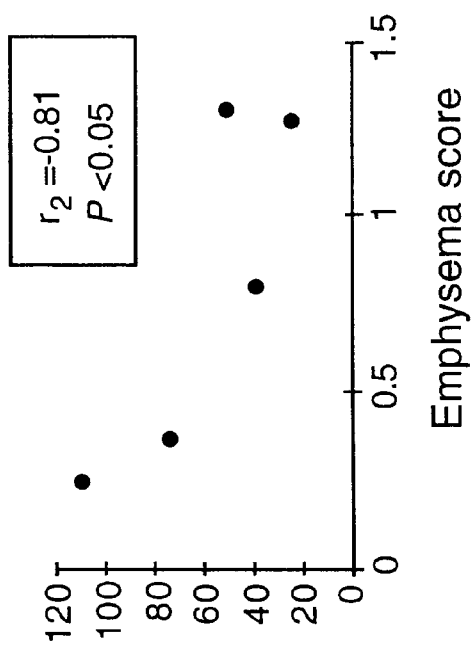

Physiological changes correlated with a semi-quantitative assessment of emphysema were also assessed histologically. In a blind study, eight sections (one per lobe) from each animal were scored as follows: 0=no emphysema; 1=mild emphysema; 2=moderate emphysema; 3=severe emphysema. A total score was determined as the average from eight sections prepared from each animal. Total lung resistance tended to increase with emphysema severity score, although this correlation was not statistically significant due to the presence of one outlier, and the small number of animals studied. Dynamic compliance did correlate inversely with emphysema severity score in a significant fashion (FIGS. 6a and 6b).

EXAMPLE 5

In Vivo Application of BLVR

Induction of emphysema in sheep, as described above, provides an excellent model in which to test both the safety and efficacy of BLVR. In the studies described below, eight sheep having emphysema were analyzed; four did not receive treatment and four were treated with BLVR. Measurements were performed: (1) at baseline prior to papain exposure; (2) eight weeks following papain exposure (at which time all animals had developed emphysema) and; (3) six weeks following either sham bronchoscopy without lung volume reduction (control) or BLVR performed with a fibrinogen-based composition (experimental). More specifically, the experimental animals were treated with a fibrinogen-based solution containing 5% fibrinogen, which was subsequently-polymerized with 1000 units of thrombin in a 5 mM calcium solution.

All animals demonstrated physiological evidence of emphysema with increased lung resistance, increased dynamic elastance, increased total lung volumes, and changes in static pressure volume relationships consistent with mild to moderate emphysema. Thus, papain therapy administered via nebulizer, as described above, caused emphysema.

Figure 7:
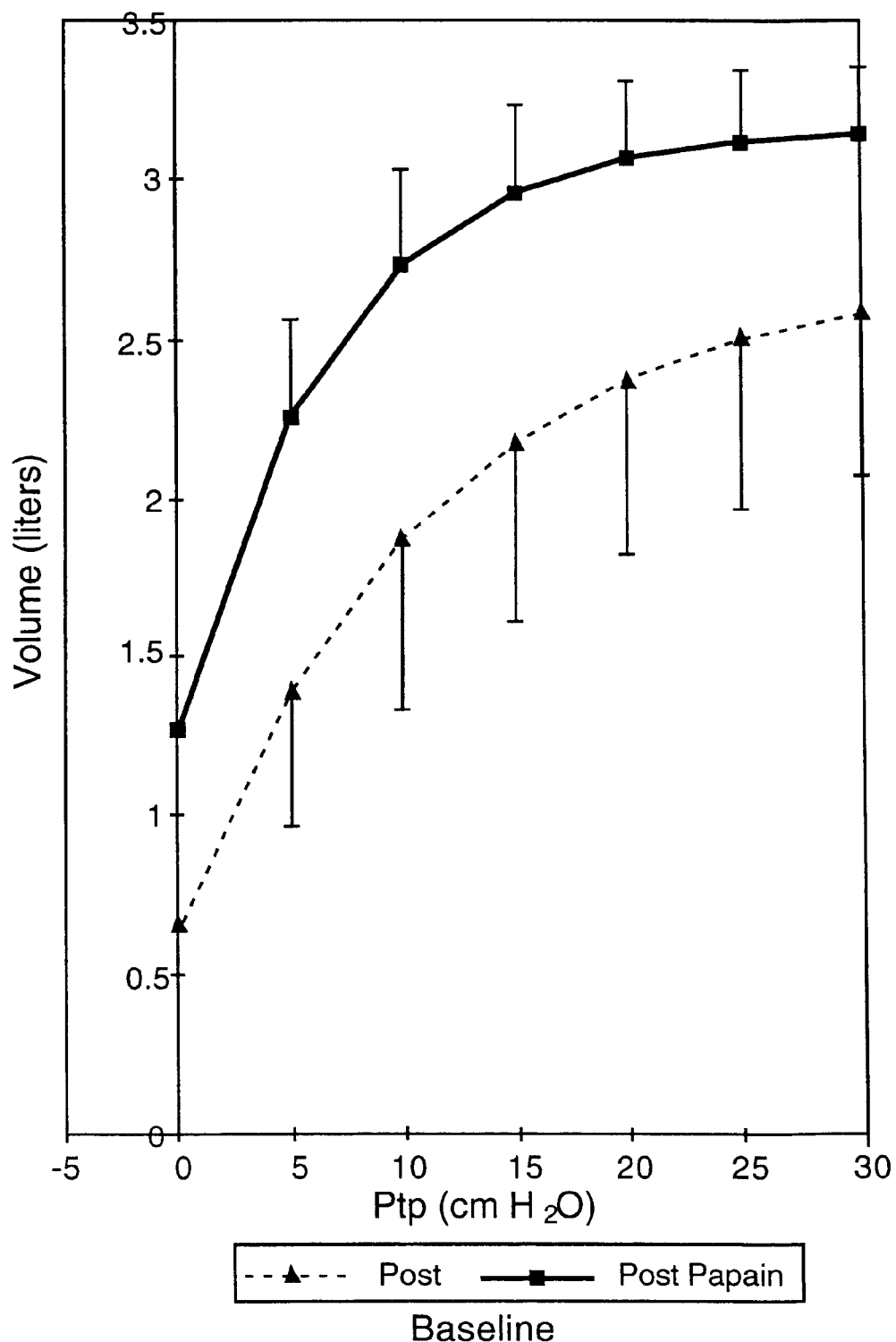
FIG. 7 is a graph illustrating static lung compliance (volume in liters vs. Ptp in cm $H_2O$) at baseline (i.e., pre-treatment) and at eight weeks following papain therapy in sheep.

After six weeks, animals with papain-induced emphysema that did not receive any therapy had persistent increases in lung resistance (125% at normal breathing frequency compared to pre-treatment baseline) and dynamic elastance (31% at normal breathing frequency compared to pre-treatment baseline). Static lung behavior remained markedly abnormal compared to baseline, with lung volumes increased 3.3% compared to pre-treatment baseline. These results are summarized below in Table 3 and shown in FIG. 7.

TABLE 3

| Treatment | RL (cm $H_2O$/L/sec) at f = 10 b/min | EL (cm $H_2O$/L) at f = 10 b/min | Raw (cm $H_2O$/L/sec) |
| --- | --- | --- | --- |
| Baseline (n = 8) | 1.71 ± 0.36 | 10.85 ± 2.78 | 0.50 ± 0.23 |
| Post-Papain (n = 8) | 3.03 ± 0.47 | 13.51 ± 3.81 | 1.17 ± 0.39 |

TABLE 3-continued

| Treatment | RL (cm H$_2$O/L/sec) at f = 10 b/min | EL (cm H$_2$O/L) at f = 10 b/min | Raw (cm H$_2$O/L/sec) |
|---|---|---|---|
| Statistical Significance | p = 0.041 | p = 0.20 | p = 0.029 |

In contrast, after six weeks, animals treated with BLVR experienced a significant reduction in airway resistance, in total lung resistance at normal breathing frequency, in total lung capacity, and in resting lung volumes. These results, which are summarized in Table 4, indicate a significant improvement in lung physiology compared to pre-volume reduction, and a significant improvement relative to untreated animals.

TABLE 4

| Experimental Group | Raw (cm H$_2$O/ L/sec) | RL (cm H$_2$O/ L/sec) at f = 10 b/min | FRC (liters) resting lung volume | TLC (liters) maximum lung volume |
|---|---|---|---|---|
| Pre-treatment volume reduction | 0.61 ± 0.31 | 3.47 ± 1.14 | 1.27 ± 0.31 | 3.31 ± 0.62 |
| Post-treatment volume reduction | 0.82 ± 0.31 | 1.85 ± 0.57 | 0.97 ± 0.21 | 2.85 ± 0.71 |
| Control following sham treatment | 1.14 ± 1.22 | 3.21 ± 0.97 | 0.80 ± 0.31 | 2.76 ± 0.49 |

Moreover, all animals treated by BLVR tolerated the procedure well. They were all able to breath without ventilator support within one hour of completion of the procedure, and were eating and drinking normally within 24 hours. One of four animals developed a fever, which lasted two days, and was easily managed with five days of intramuscular antibiotic therapy. No other complications were noted. Thus, the plysiological response to BLVR was very positive.

Other Embodiments

While the compositions and methods of the present invention are particularly suitable for use in humans, they can be used generally to treat any mammal (e.g., farm animals such as horses, cows, and pigs and domesticated animals such as dogs and cats).

In addition, the compositions described above can be usefully applied to a variety of tissues other than the lung. For example, they can be applied to seal leaks of cerebrospinal fluid; to seal anastomoses of native and prosthetic vascular grafts (including those associated with the implantation of prosthetic valves such as mitral valves); in diagnostic or interventional procedures or endoscopic or orthopedic procedures involving the intentional or accidental puncture of a vessel wall; in plastic surgery; and in highly vascular cut tissue (e.g., the kidneys, liver, and spleen). The compositions described above can also be applied to accelerate healing in diabetics and to treat septic wounds of longstanding resistance to standard approaches, including antibiotic-resistant bacterial infections.

What is claimed is:

1. A non-surgical method of reducing lung volume in a patient, the method comprising:
   (a) collapsing a target region of the patient's lung; and
   (b) administering, by way of the patient's trachea, to the target region of the patient's lung:
      (i) a first composition comprising 3–12% fibrinogen and
      (ii) a second composition comprising a fibrinogen activator, whereafter one portion of the target region adheres to another portion of the target region, thereby reducing the patient's lung volume.

2. The method of claim 1, wherein the first composition comprises about 10% fibrinogen.

3. The method of claim 1, wherein the fibrinogen is autologous fibrinogen.

4. The method of claim 1, wherein the fibrinogen activator is thrombin, a thrombin receptor agonist, or batroxobin.

5. The method of claim 1, wherein the first composition or the second composition further comprises an antibiotic.

6. The method of claim 1, wherein the target region is collapsed by blocking air flow into or out of the region.

7. The method of claim 1, wherein the target region is collapsed by lavaging the target region with an antisurfactant.

8. The method of claim 1, wherein the method is performed using a bronchoscope.

9. The method of claim 1, wherein the patient is a human patient.

10. The method of claim 1, wherein the patient has emphysema.

11. The method of claim 1, wherein the patient has suffered a traumatic injury to the lung.

* * * * *